US012806542B2

(12) United States Patent
Andrade et al.

(10) Patent No.: US 12,806,542 B2
(45) Date of Patent: Nov. 24, 2026

(54) PROCESS AND SYSTEM FOR DEHYDRATING A PRODUCT STREAM IN ETHANOL PRODUCTION

(71) Applicant: Whitefox Technologies Limited, London (GB)

(72) Inventors: Virginia Andrade, Calgary (CA); Jin Ming Zhou, Calgary (CA); Stephan Rudiger Blum, Calgary (CA)

(73) Assignee: Whitefox Technologies Limited, London (GB)

( * ) Notice: Subject to any disclaimer, the term of this patent is extended or adjusted under 35 U.S.C. 154(b) by 400 days.

(21) Appl. No.: 18/377,975

(22) Filed: Oct. 9, 2023

(65) Prior Publication Data

US 2024/0033652 A1 Feb. 1, 2024

Related U.S. Application Data

(60) Division of application No. 17/135,213, filed on Dec. 28, 2020, now Pat. No. 11,779,858, which is a (Continued)

(51) Int. Cl.
*B01D 3/14* (2006.01)
*B01D 1/26* (2006.01)
(Continued)

(52) U.S. Cl.
CPC ............... *B01D 3/146* (2013.01); *B01D 1/26* (2013.01); *B01D 1/28* (2013.01); *B01D 3/002* (2013.01);
(Continued)

(58) Field of Classification Search
None
See application file for complete search history.

(56) References Cited

U.S. PATENT DOCUMENTS 4,217,178 A 8/1980 Katzen et al.
4,306,942 A 12/1981 Brush et al.
(Continued)

FOREIGN PATENT DOCUMENTS

CN 1802194 A 7/2006
CN 104262090 1/2015
(Continued)

OTHER PUBLICATIONS

Schaschke, Carl. (2014). Dictionary of Chemical Engineering—distillation. Oxford University Press. Retrieved from <br>https://app.knovel.com/hotlink/pdf/id:kt00TW5IA6/dictionary-chemical-engineering/distillation (Year: 2014).*

(Continued)

*Primary Examiner* — Gabriel E Gitman
(74) *Attorney, Agent, or Firm* — K&L Gates LLP

(57) ABSTRACT

The present disclosure provides processes and systems for ethanol production. In one embodiment, a first beer column receives a first portion of a feed mixture including ethanol and water to form a first beer column bottom stream and a first beer column vaporous overhead stream. A beer column receives a second portion of the feed mixture. A first portion of the first beer column bottom stream is forwarded to a first beer column reboiler. A second portion of the first beer column bottom stream is forwarded to a plurality of evaporators. A condensed portion of the first beer column vaporous overhead stream is forwarded to a stripper column. The stripper column forms a feed stream, which is contacted with a separation system, thereby forming a permeate and a retentate. The permeate is forwarded directly to at least one selected from the first beer column and the stripper column.

9 Claims, 18 Drawing Sheets

Related U.S. Application Data continuation of application No. 16/405,374, filed on May 7, 2019, now Pat. No. 10,874,956.

(60) Provisional application No. 62/667,933, filed on May 7, 2018.

(51) Int. Cl.

| | |
|---|---|
| ***B01D 1/28*** | (2006.01) |
| ***B01D 3/00*** | (2006.01) |
| ***B01D 15/20*** | (2006.01) |
| ***B01D 61/36*** | (2006.01) |
| ***C07C 29/80*** | (2006.01) |
| ***C12P 7/06*** | (2006.01) |
| *C07C 31/08* | (2006.01) |

(52) U.S. Cl.

CPC ............. *B01D 3/007* (2013.01); *B01D 3/145* (2013.01); *B01D 3/148* (2013.01); *B01D 15/203* (2013.01); *B01D 61/3631* (2022.08); *B01D 61/3641* (2022.08); *C07C 29/80* (2013.01); *C12P 7/06* (2013.01); *B01D 3/005* (2013.01); *C07C 31/08* (2013.01)

(56) References Cited

U.S. PATENT DOCUMENTS

| | | | | |
|---|---|---|---|---|
| 4,326,036 | A | 4/1982 | Hayes | |
| 4,340,446 | A | 7/1982 | Crawford | |
| 4,405,409 | A | 9/1983 | Tusel et al. | |
| 4,407,662 | A | 10/1983 | Ginder | |
| 4,422,903 | A | 12/1983 | Messick et al. | |
| 4,428,799 | A | 1/1984 | Standiford | |
| 4,978,430 | A | 12/1990 | Nakagawa et al. | |
| 5,105,029 | A | 4/1992 | Ninomiya et al. | |
| 5,124,004 | A | 6/1992 | Grethlein et al. | |
| 7,470,348 | B2 | 12/2008 | Seiki et al. | |
| 7,572,353 | B1 | 8/2009 | Vander Griend | |
| 7,594,981 | B2 | 9/2009 | Ikeda | |
| 7,699,961 | B2 | 4/2010 | Ikeda et al. | |
| 7,732,173 | B2 | 6/2010 | Mairal et al. | |
| 7,744,727 | B2 | 6/2010 | Blum et al. | |
| 7,867,365 | B2 | 1/2011 | Brown | |
| 7,922,872 | B2 | 4/2011 | Kihara et al. | |
| 8,103,385 | B2 | 1/2012 | Macharia | |
| 8,128,787 | B2 | 3/2012 | Wynn et al. | |
| 8,128,826 | B2 | 3/2012 | Plante et al. | |
| 8,129,573 | B2 | 3/2012 | Kikuchi et al. | |
| 8,142,662 | B2 | 3/2012 | Osora et al. | |
| 8,425,734 | B2 | 4/2013 | Goel et al. | |
| 8,585,904 | B2 | 11/2013 | Osora et al. | |
| 8,858,798 | B2 | 10/2014 | Osora et al. | |
| 9,149,769 | B2 | 10/2015 | Seiki et al. | |
| 9,194,623 | B2 | 11/2015 | Kihara et al. | |
| 9,925,476 | B2 | 3/2018 | Crawford et al. | |
| 10,118,107 | B1 | 11/2018 | Kwik et al. | |
| 10,874,956 | B2 | 12/2020 | Andrade et al. | |
| 2006/0070867 | A1 | 4/2006 | Ikeda | |
| 2007/0000769 | A1 | 1/2007 | Brown | |
| 2007/0131533 | A1 | 6/2007 | Blum et al. | |
| 2008/0135396 | A1 | 6/2008 | Blum | |
| 2008/0207959 | A1 | 8/2008 | Plante et al. | |
| 2009/0004713 | A1 | 1/2009 | Wynn et al. | |
| 2009/0057128 | A1 | 3/2009 | Vane et al. | |
| 2009/0117631 | A1 | 5/2009 | Cote et al. | |
| 2009/0215139 | A1 | 8/2009 | Datta et al. | |
| 2009/0301970 | A1 | 12/2009 | Noel | |
| 2010/0051441 | A1 | 3/2010 | Vane et al. | |
| 2010/0219128 | A1 | 9/2010 | Seiki et al. | |
| 2010/0314320 | A1 | 12/2010 | Osora et al. | |
| 2011/0046425 | A1* | 2/2011 | Gartside ............... | C07C 11/107 585/315 |
| 2011/0108409 | A1 | 5/2011 | Brown | |
| 2011/0130598 | A1 | 6/2011 | Huang et al. | |
| 2011/0315541 | A1 | 12/2011 | Xu | |
| 2012/0137727 | A1 | 6/2012 | Huang et al. | |
| 2013/0015052 | A1 | 1/2013 | Vane et al. | |
| 2013/0165678 | A1 | 6/2013 | Kohl et al. | |
| 2013/0309738 | A1* | 11/2013 | Barr ....................... | C12M 29/18 29/401.1 |
| 2015/0087041 | A1 | 3/2015 | Parten | |
| 2016/0107964 | A1 | 4/2016 | Matsukata et al. | |
| 2016/0324205 | A1 | 11/2016 | Herbst | |
| 2017/0203230 | A1* | 7/2017 | Raiser ..................... | C07C 29/80 |
| 2017/0204030 | A1 | 7/2017 | Maeda et al. | |
| 2019/0184378 | A1* | 6/2019 | Zhu .......................... | B01J 23/72 |

FOREIGN PATENT DOCUMENTS

| | | |
|---|---|---|
| CN | 104610018 | 5/2015 |
| JP | 2016047530 | 4/2016 |
| WO | 2016088134 | 6/2016 |

OTHER PUBLICATIONS

Roy, Christian; "Vaperma Siftek Membrane for Ethanol Refining: A General Presentation"; Vaperma, Inc.; Mar. 2010; (32 pages).

Gabardo, Helio; "Dehydration of Ethanol Via Membrane Polymeric Siftek"; Dec. 4, 2009; (34 pages).

Search Report and Written Opinion dated Oct. 16, 2019 issued for International PCT Application No. PCT/IB2019/000546.

CN104610018A_ENG (Espacenet machine translation of Miao) (Year 2015).

CN104262090A_ENG (Espacenet machine translation of Miao) (Year 2015).

* cited by examiner

PROCESS AND SYSTEM FOR DEHYDRATING A PRODUCT STREAM IN ETHANOL PRODUCTION

PRIORITY CLAIM

The present disclosure is a continuation of U.S. patent application Ser. No. 17/135,213 filed on Dec. 28, 2020 which is a continuation of U.S. patent application Ser. No. 16/405,374 filed on May 7, 2019 which claims priority to U.S. Provisional Patent Application No. 62/667,933, entitled “Process and System for Dehydrating a Product Stream in Ethanol Production,” filed May 7, 2018, the entire contents of each of which are hereby incorporated by reference and relied upon.

BACKGROUND

Various processes and systems have been used for producing ethanol from feedstock. For example, in some prior systems, ethanol is produced by fermentation, yielding a stillage (beer) with an ethanol concentration of up to 18%, which is subsequently concentrated in three steps: (1) distillation in a beer column, increasing the ethanol concentration up to 65%, followed by (2) processing in a stripper/rectifier column further increasing the ethanol concentration to around 90 vol %, and (3) a molecular-sieve-based dehydration (also referred to as pressure swing adsorption) to a target ethanol concentration of 99.0 to 99.95 vol %. In the stripper/rectifier column, a mixture of high boiling components including propanol, butanol, and isomeric pentanols (also referred to as fusel oil) needs to be removed in a side draw to avoid accumulation therein.

SUMMARY

According to one non-limiting aspect of the present disclosure, an example embodiment of a method for dehydrating a product stream in ethanol production is described. The example method includes, receiving, at a first beer column, a first portion of a feed mixture including ethanol and water to form a first beer column bottom stream and a first beer column vaporous overhead stream. A second portion of the feed mixture is received at a second beer column. The second beer column is operated at a higher pressure than the first beer column to form a second beer column bottom stream and a second beer column vaporous overhead stream. A first portion of the first beer column bottom stream is forwarded to a first beer column reboiler. A second portion of the first beer column bottom stream is forwarded to a plurality of evaporators. At least a portion of the second beer column bottom stream is forwarded to a second beer column reboiler. The first beer column vaporous overhead stream is condensed. A condensed portion of the first beer column vaporous overhead stream is forwarded to a stripper column. The stripper column forms a feed stream. The feed stream is contacted with a separation system, thereby forming a permeate and a retentate. At least a portion of the permeate is forwarded directly to at least one selected from the first beer column and the stripper column.

According to another non-limiting aspect of the present disclosure, another example embodiment of a method for dehydrating a product stream in ethanol production is described. The example method includes distilling a feed mixture including ethanol and water with one or more distillation units to form a distillation unit bottom stream and a vaporous overhead stream. A molecular sieve unit is contacted with a byproduct stream comprising at least a portion of the vaporous overhead stream, thereby forming a product stream and a regenerate stream. The regenerate stream is contacted with a separation system comprising a stripper column and a membrane, thereby forming a permeate and a retentate. At least a portion of the product stream is forwarded to a plurality of evaporators. The plurality of evaporators include at least a first evaporator and a second evaporator connected without any intervening evaporators therebetween. Each of the plurality of evaporators forms a vegetal steam, and the vegetal steam is forwarded from the first evaporator to the second evaporator.

According to another non-limiting aspect of the present disclosure, an example embodiment of a system for dehydrating a product stream in ethanol production is described. The example system includes one or more distillation units configured to receive a feed mixture including ethanol and water, to form a distillation unit bottom stream and a vaporous overhead stream. A molecular sieve unit is configured to contact a byproduct stream comprising at least a portion of the vaporous overhead stream. The molecular sieve unit is configured to form a product stream and a regenerate stream. A separation system includes a stripper column and a membrane. The separation system is configured to contact the regenerate stream, thereby forming a permeate and a retentate. A plurality of evaporators include at least one selected from a 2-effect evaporator, a 4-effect evaporator, a 6-effect evaporator, and an 8-effect evaporator. The plurality of evaporators include at least a first evaporator and a second evaporator connected without any intervening evaporators therebetween. Each of the plurality of evaporators is configured to form a vegetal steam. The vegetal steam is forwarded from the first evaporator to the second evaporator.

BRIEF DESCRIPTION OF THE DRAWINGS

Features and advantages of the processes and systems described herein may be better understood by reference to the accompanying drawings in which.

The reader will appreciate the foregoing details, as well as others, upon considering the following detailed description of certain non-limiting embodiments of processes and systems according to the present disclosure. The reader may also comprehend certain of such additional details upon using the processes and systems described herein.

DETAILED DESCRIPTION

Prior systems for producing ethanol from feedstock typically require molecular sieve units (MSUs) for dehydrating the feed vapor coming from the stripper/rectifier column or a dedicated vaporizer. The MSUs include two or three beds filled with zeolite pellets, which adsorb water to produce anhydrous vapor until they are saturated with water. While the first bed undergoes a regeneration cycle, the feed vapor coming from the stripper/rectifier column can be switched to a second bed for continued dehydration. Desorption/depressurization with or without redirecting a portion of freshly dehydrated alcohol into the first bed to remove the water from the saturated zeolite beads, forms a regenerate stream (also referred to as MSU Regen). Due to the water desorption, the regenerate stream has an ethanol concentration between 50 and 80 vol %, and needs to be recycled to upstream distillation for reprocessing. This operation has a number of disadvantages. For example, as a large portion of ethanol is continuously recycled, (1) capacity in the upstream distillation is used up for dehydrating the MSU Regen, (2) capacity in the MSU itself is used up to essentially dehydrate its own regenerate stream for recycling, and (3) additional energy or steam and cooling water are required for the reprocessing of the MSU Regen. Thus, there has developed a need for processes and systems that overcome the limitations of prior processes for ethanol production.

Figure 1:
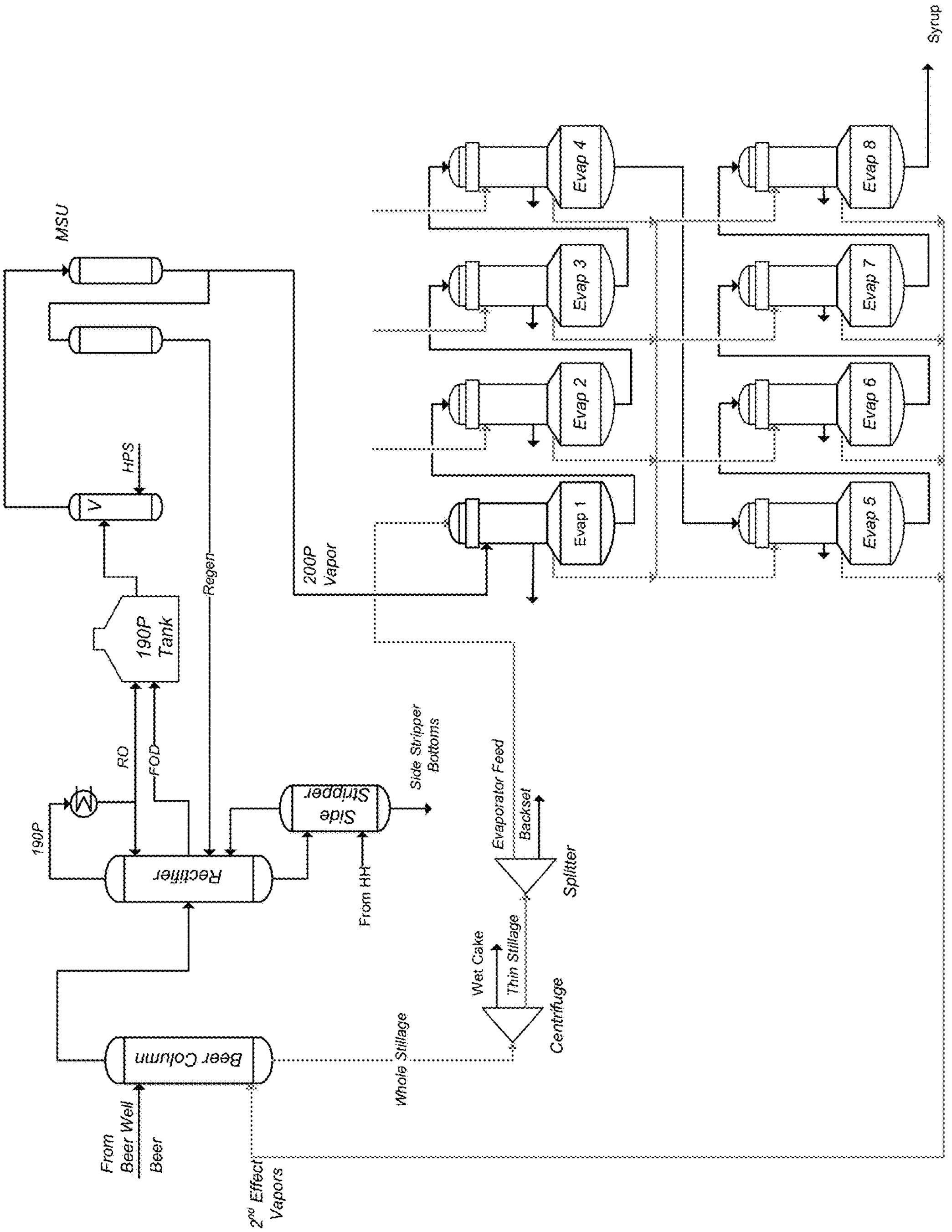
FIG. 1 is a schematic illustration of a system for ethanol production in related art.

Referring to FIG. 1, prior ethanol production processes typically include (1) distillation with beer column, rectifier and side stripper, (2) a 190 proof tank, (3) dehydration with vaporizer (V) and molecular sieve unit (MSU), (4) a centrifuge, (5) a splitter and (6) evaporation with 4 double effect evaporators (Evap 1-Evap 8). Beer with an ethanol concentration of 2% to 20% coming from the beer well is pumped into the beer column together with a vegetal steam coming from the second evaporator effect (direct steam injection) to be separated into the beer column overheads containing up to 65% ethanol and 35% water and whole stillage containing approx. 90% water, and approx. 10% suspended (fiber) and dissolved solids (salts). The beer column overheads are fed into the rectifier to be separated into the rectifier overheads with approx. 93% ethanol and 7% water, the fusel oil draw (FOD) containing ethanol, isomeric pentanols and water and the side stripper bottoms containing essentially only water. The rectifier overheads are condensed in the 190 proof condenser and sent to the 190 proof tank together with the FOD. The 190 proof mixture is then pumped into the vaporizer (V) which is heated with high pressure steam (HPS). The 190 proof vapors are then sent at a pressure of 60-85 psig to the mole sieves to be polished to an ethanol concentration of 99% and higher (200 proof vapor). The heat in the 200 proof vapor is being recovered in the first evaporator (Evap 1). The MSU regenerate (Regen) is being sent back to the rectifier.

Figure 2:
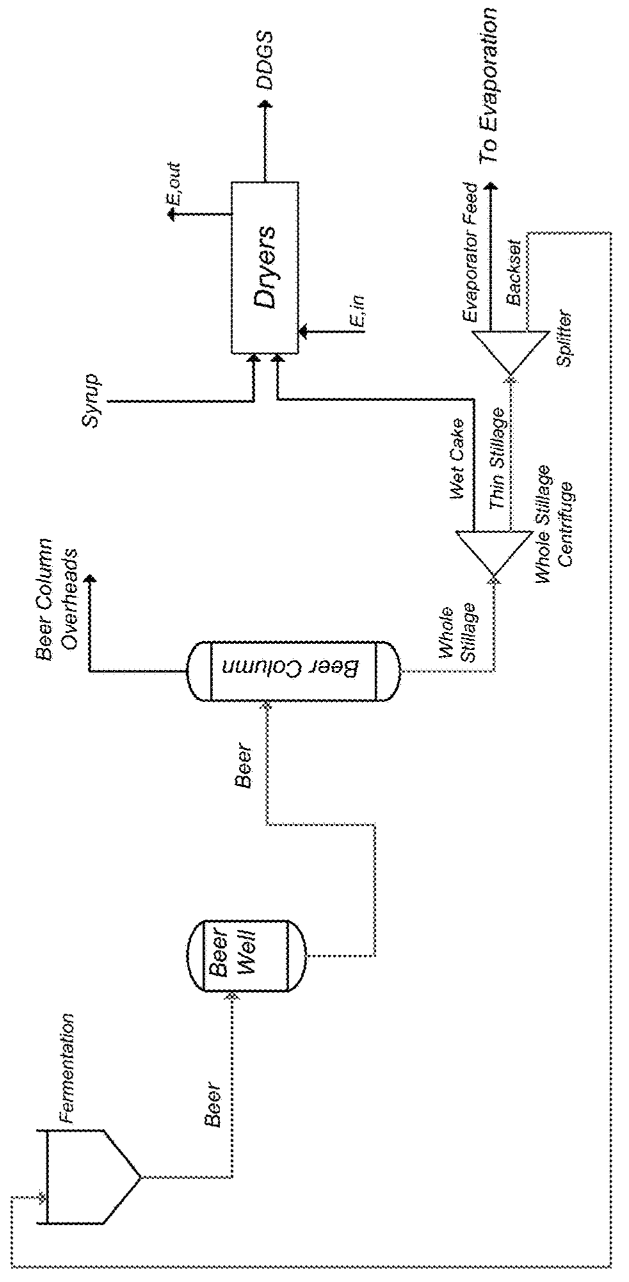
FIG. 2 is a schematic illustration of another system for ethanol production in related art.

With continuing reference to FIG. 1, the whole stillage with i) the majority of the process water introduced with the beer plus ii) the condensed VS2 is illustrated with a flow of 200,000 lbs/h. The stream is separated in the centrifuge into the wet cake and the thin stillage. Referring to FIG. 2, the wet cake will be transferred to the dryer section. The thin stillage will be split into two streams—i) the evaporator feed and the backset further described in FIG. 2. The evaporator feed is now pumped into a series of evaporators. The solids are being concentrated as they travel through a series of evaporators (typically eight evaporators) to exit the eighth evaporator (Evap 8) as syrup with a solids concentration of approx. 39% syrup. The energy to the evaporators is supplied through the 200 proof vapor to the first evaporator (Evap 1) and low pressure steam to the second evaporator (Evap 2), the third evaporator (Evap 3) and the fourth evaporator (Evap 4) producing a first effect vegetal steam at a pressure of 14.7 psia which is sent to a second effect at 9.6 psia producing a second vegetal steam before it is re-injected into the beer column.

The term "vegetal steam" as used herein indicates that this is a vaporous process water stream which may contain various contaminants as opposed to primary steam which can be condensed and returned to the boiler house. FIG. 1 illustrates a large water recycle loop which roughly amounts to 25% of the whole stillage stream. The extra water being recycled substantially increases various downstream sections, mainly the centrifuge, the evaporation section, the drying section (via wet cake), and fermentation (via backset).

Referring to FIG. 2, other portions of an ethanol production plant are illustrated. Beer is pumped from the fermentation into the beer well and from here to the beer column which produces the beer column overheads to be sent to the rectifier. The whole stillage is sent to a centrifuge to be split into the wet cake and the thin stillage. In the subsequent splitter the thin stillage is separated into the evaporator feed and the backset which is recycled back to the fermentation. The wet cake and the syrup from the evaporation section is sent to a dryer section where energy is injected (E, in) to drive out the remaining moisture producing a dry final DDGS product (distiller's dried grains and solubles). The dryer energy can be provided in various forms, including pure natural gas, steam and sweep air. Typical dryer types are rotary direct-fired dryers, rotary indirect-fired dryers, ring dryers, rotary steam tube dyers and superheated steam dryers, using hot streams from other plant sections such as thermal oxidizers and regenerative thermal oxidizers. All dryers produce valuable off-heat (E, out) which can be recovered in other sections of the plant.

With continuing reference to FIG. 2, the backset stream represents a large solids and water recycle via the cook and liquefaction section to the fermentation. There are some benefits provided, including i) reducing evaporator duty, ii) pH adjustments and iii) recycle of nutrients. On the other hand there are numerous negative impacts of backset recycling, including i) cycling up the concentration of fermentation inhibitors (e.g. lactic acid, acetic acid, sodium) and suspended solids fines, increasing syrup viscosity and ii) increasing dryer duty.

There can be numerous drawbacks with the design illustrated in FIG. 1. The main drawback is that the entire system is auto-integrated by linking the beer column operation with two functions of the evaporation. The steam demand of the beer column is determined by its capacity. The evaporation's two functions are to i) produce a syrup concentration of approx. 39% and ii) to generate the required steam for the beer column. The resulting variable is the backset flow which is adjusted to balance the system. The backset is a recycle loop back to the cook section, determined by the backset split, defined as the ratio of the backset flow and the thin stillage flow. Ideally, the backset split should be between 8-25%, and not higher than 50%. Therefore, the two parameters i) beer column capacity and ii) syrup concentration dictate the steam supply to the evaporation and thus the backset split.

Secondly, the energy efficiency of the system is determined by the operation of various plant sections at different pressures, i.e. the dehydration at high pressure (60-85 psia), the evaporation under mid pressure (9.6/14.7 psia) and distillation under vacuum (6-8 psia). However, the energy cascade is broken between the rectifier and the vaporizer as the 190 proof vapor must be condensed under vacuum and pumped to the vaporizer to be re-vaporized under pressure. This condensation/re-vaporization step is an inherently energy intensive step.

Thirdly, large water/solids recycle streams take away potential capacity of the plant equipment causing capacity bottlenecks.

Fourthly, due to continuous efforts to increase production capacity beer columns are increasingly overloaded, thus becoming the main bottleneck of the entire facility.

Fifthly, overloading beer columns and rectifiers can result in unintended fusel oil discharge into the rectifier bottoms leading to recycling of stray fuel oils into the fermentation causing yeast poisoning.

The present disclosure, in part, is directed to processes and systems for dehydrating a product stream in ethanol production to reduce steam consumption and backset split without reducing capacity and/or syrup concentration. A pressure cascaded system includes two beer columns and a stripper column which directly feeds a vapor permeation membrane. The distillation system is contacted with other sections of the plant for heat integration. In certain non-limiting embodiments, heat is exchanged between the distillation system and the evaporation section. In certain non-limiting embodiments, heat is exchanged between the distillation system and the dryer section. In certain non-limiting embodiments, heat is exchanged between the distillation system and the RT/TO section. In certain non-limiting embodiments, heat is exchanged between the distillation system and the CHP section. In certain non-limiting embodiments, the ethanol process includes one beer column, one rectifier/side-stripper, and a vaporizer that produces a vapor that directly feeds a vapor permeation membrane. The distillation system is contacted with other sections of the plant for heat integration.

Figure 3:
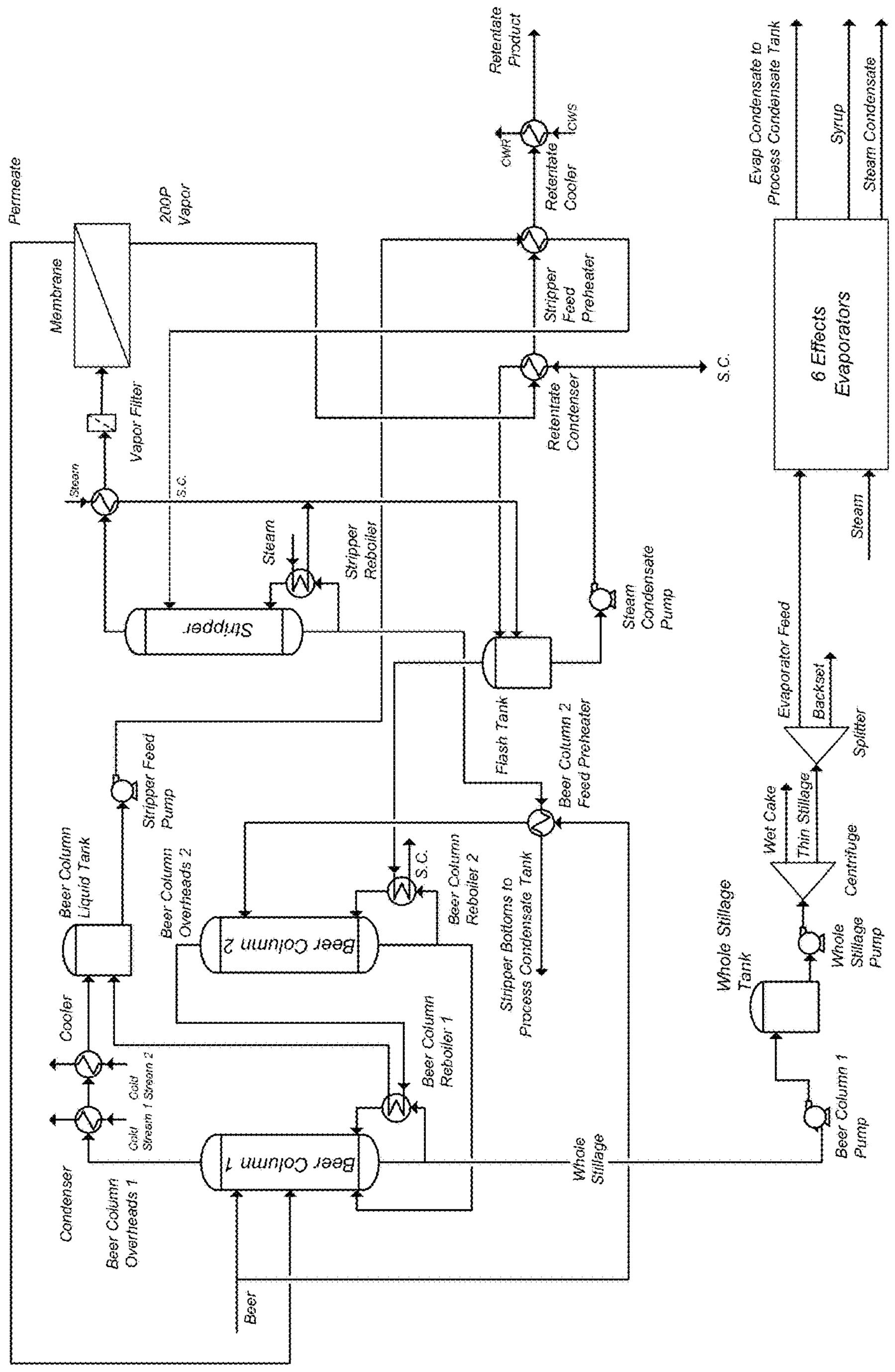
FIG. 3 is a schematic illustration of a non-limiting example embodiment of a system for dehydrating a product stream in ethanol production according to the present disclosure.

Referring to FIG. 3, the illustrated embodiment of the system or production plant for dehydrating a product stream in ethanol production includes two parallel beer columns—i) a vacuum beer column (Beer Column 1, operating between 3 and 11 psia) and ii) a mid pressure beer column (Beer Column 2, operating between 14.7 and 35 psia). Although FIG. 3 illustrates the system as including two beer columns, in other embodiments, the system may include three or more beer columns. Depending on the usage requirements or preferences for the particular system, a system that includes a single beer column may not provide the requisite pressure cascade, as further explained below.

In certain non-limiting embodiments, the heat in both beer column overheads (Beer Column Overhead 1, Beer Column Overhead 2) can be recovered through condensation in the condenser and the Beer Column 1 Reboiler before being pumped into the high-pressure stripper, operating between 40 and 85 psia. The stripper produces a vapor with an ethanol concentration of 60% to 95%, which is being directed to a membrane section that produces a water free ethanol product (200 proof) and a water rich permeate with an ethanol concentration between 1 and 60%.

In certain non-limiting embodiments, the membrane is a polymer membrane built on a hollow fiber backbone. In certain non-limiting embodiments, a selective layer is placed on either the outside (shell side) or inside (lumen side) of the hollow fibers. In other embodiments, the membrane may assume any other form, for example tubular membranes including zeolites as adsorbents or spiral wound membranes, so long as the membrane can dehydrate the membrane feed vapor to certain water contents depending on the usage requirements or preferences for the particular system. In certain non-limiting embodiments, the stripper/membrane can be installed to new systems at final assembly, or retrofitted to existing plants including plants that use extractive distillation with such separation systems.

In the illustrated embodiment the energy contained in the retentate is recuperated in the Beer Column 2 Reboiler via retentate condenser and flash tank and the energy contained in the permeate is recovered through direct injection into the first beer column (Beer Column 1). Alternatively, the permeate can be condensed in a dedicated permeate condenser and pumped into either the first beer column (Beer Column 1) or the second beer column (Beer Column 2) depending on permeate concentration.

Figure 4:
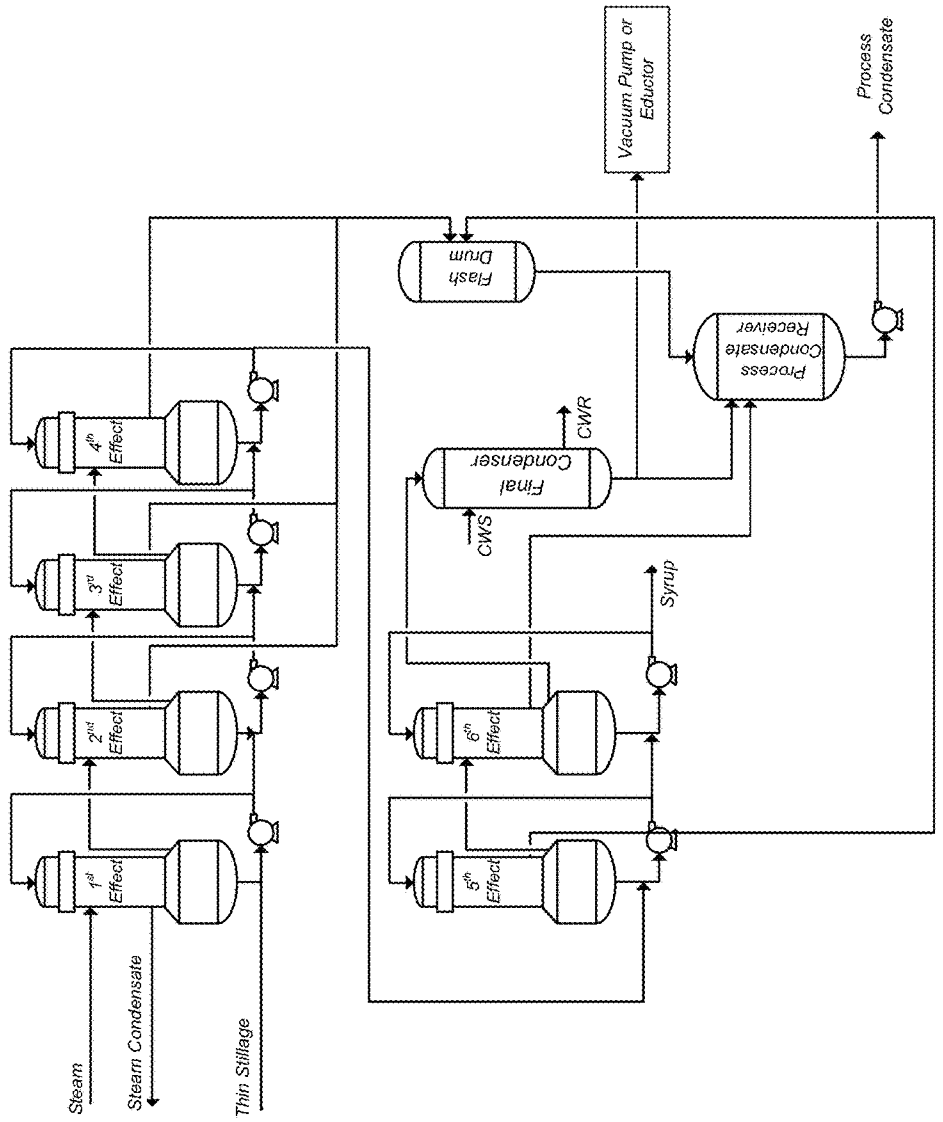
FIG. 4 is a schematic illustration of another non-limiting example embodiment of a system for dehydrating a product stream in ethanol production according to the present disclosure.
Figure 5:
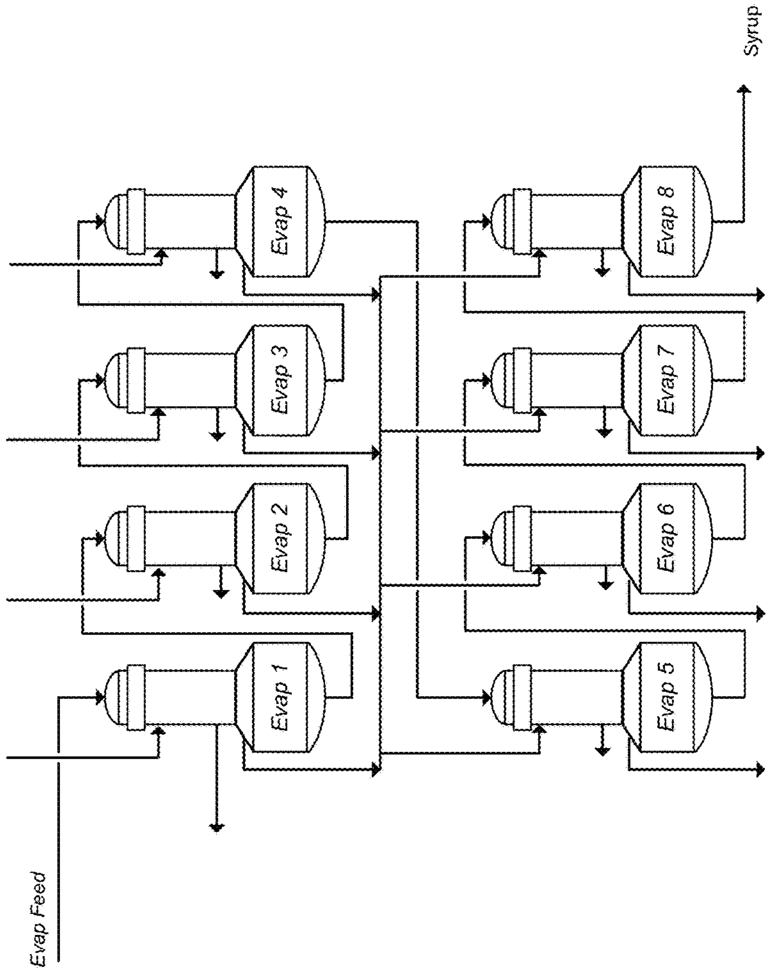
FIG. 5 is a schematic illustration of 2-effect evaporators of a non-limiting example embodiment of a system for dehydrating a product stream in ethanol production according to the present disclosure.
Figure 6:
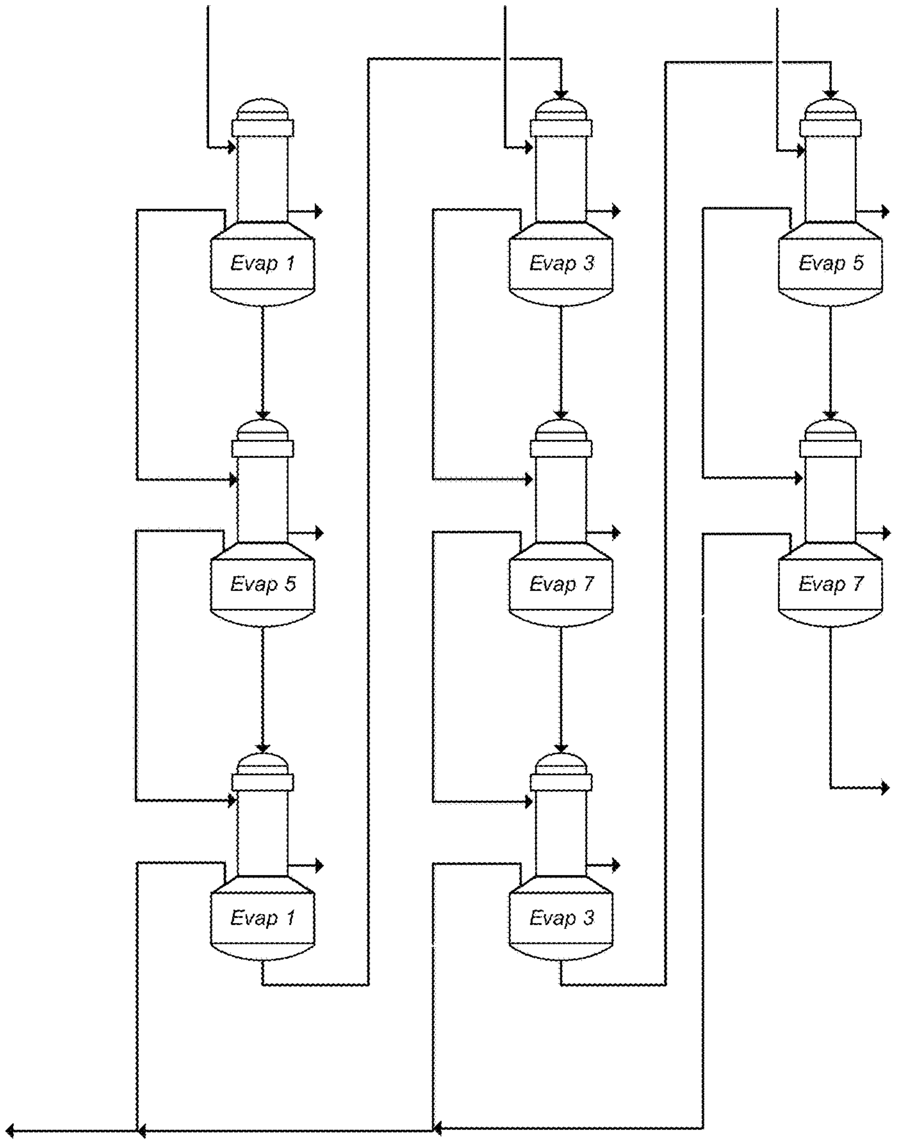
FIG. 6 is a schematic illustration of 3-effect evaporators of a non-limiting example embodiment of a system for dehydrating a product stream in ethanol production according to the present disclosure.
Figure 7:
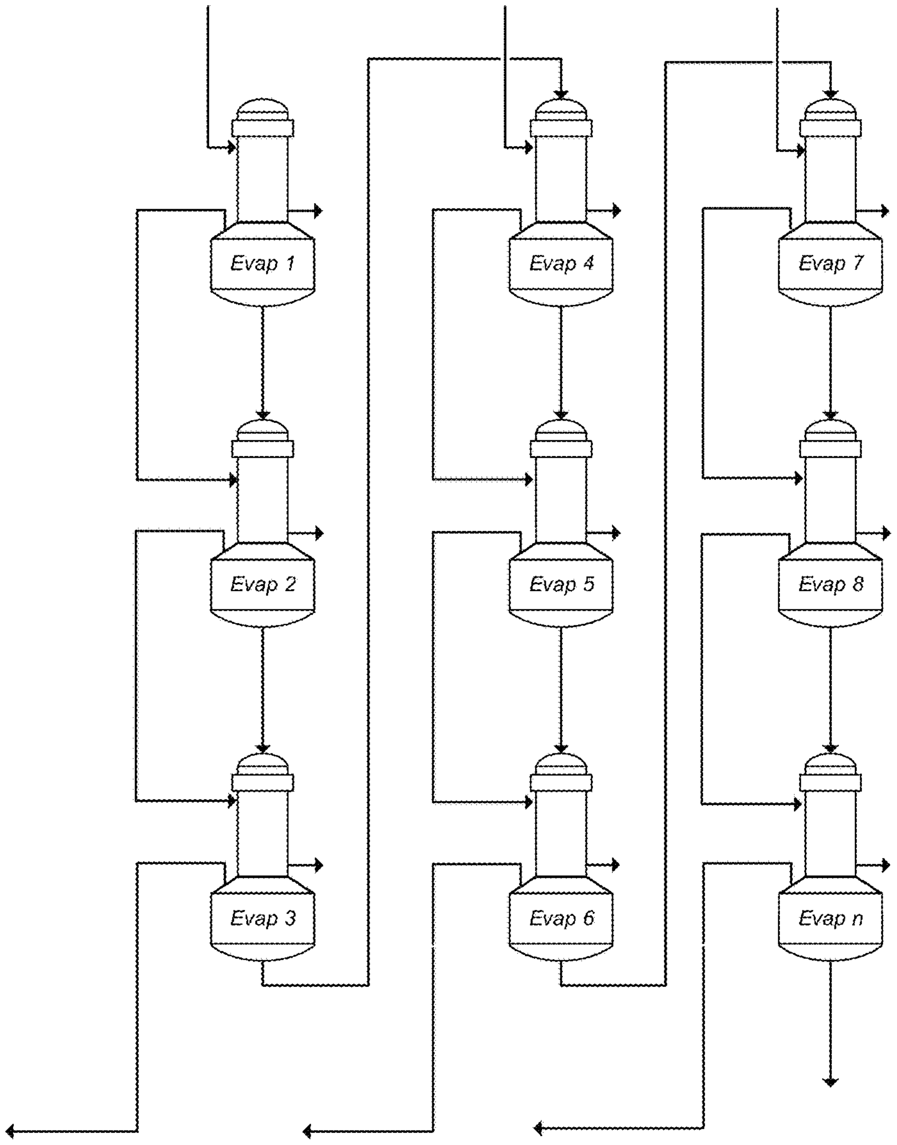
FIG. 7 is a schematic illustration of 3-effect evaporators of another non-limiting example embodiment of a system for dehydrating a product stream in ethanol production according to the present disclosure.
Figure 8:
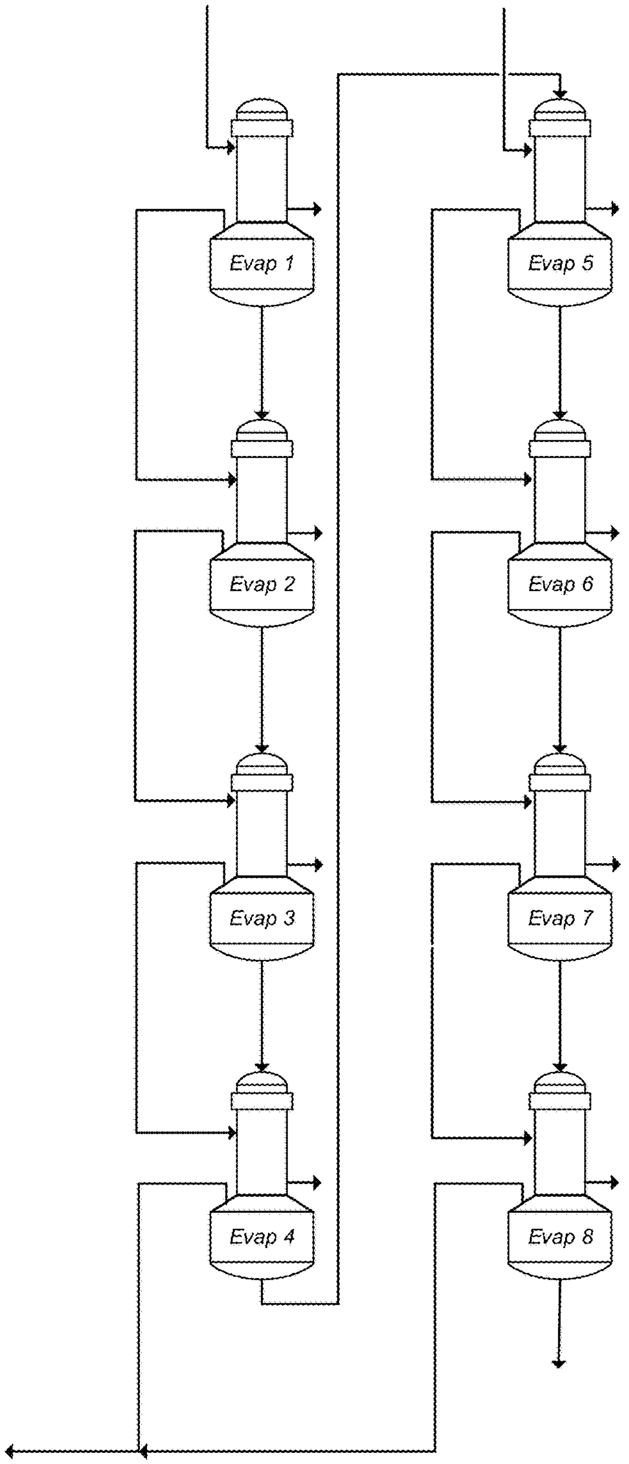
FIG. 8 is a schematic illustration of 4-effect evaporators of a non-limiting example embodiment of a system for dehydrating a product stream in ethanol production according to the present disclosure.
Figure 9:
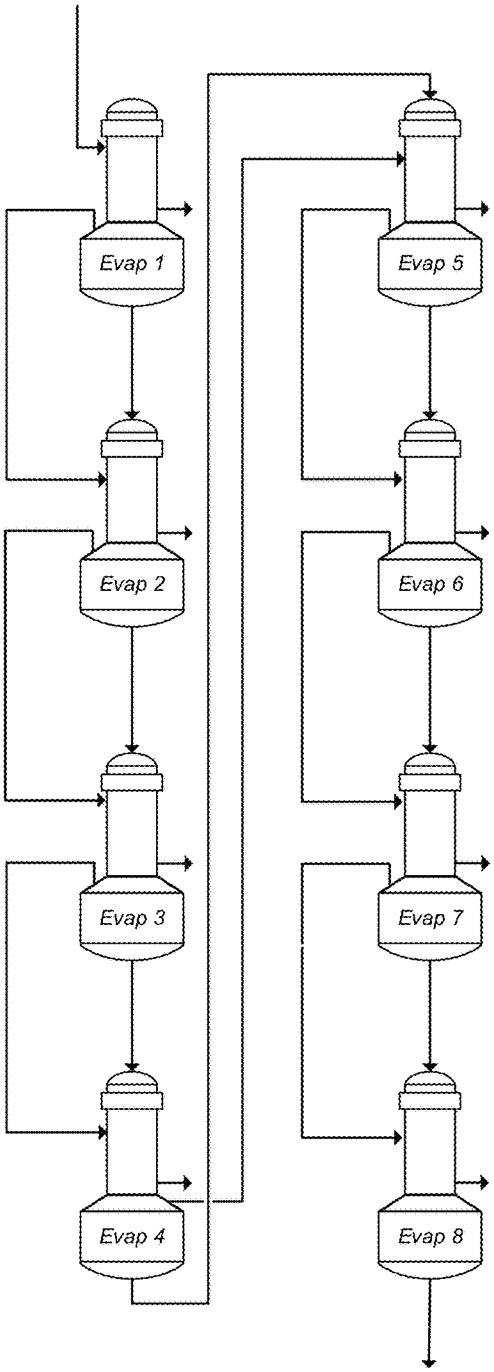
FIG. 9 is a schematic illustration of an 8-effect evaporation section of a non-limiting example embodiment of a system for dehydrating a product stream in ethanol production according to the present disclosure.

In the embodiment illustrated in FIG. 3, as both beer columns use reboilers, there is no Direct Steam Injection (DSI), which reduces the mass flow of the whole stillage by up to 25%. In certain non-limiting embodiments, DSI may not be fully eliminated as the optimum solution may favour a combination of direct steam injection and the use of beer column reboilers. Stated slightly differently, both beer columns may use both i) reboilers and ii) DSI. Reducing the amount of DSI can have a significant impact on subsequent separation steps allowing for adjustment of i) the wet cake/thin stillage split of the centrifuge operation and ii) the evaporator feed/backset split. The reduced water load can lead to a reduction of evaporator capacity, potentially eliminating two evaporators, shown as 6-effect evaporators (FIG. 4). Depending on the usage requirements or preferences for the particular system, the evaporators can be rebalanced to operate in any combination possible, e.g. as 2-effect evaporators (FIG. 5), 3-effect evaporators (FIGS. 6-7 by adding additional evaporators), 4-effect evaporators (FIG. 8), or one 8-effect evaporation section (FIG. 9). Alternatively, the remaining evaporators can be used to reduce the backset to the fermentation. A benefit of the processes and systems for dehydrating a product stream in ethanol production according to the present disclosure is that the arrangement with two beer columns would allow to de-bottleneck the existing Beer Column 1 by repurposing the existing rectifier/side stripper as Beer Column 2, which essentially allows doubling the capacity of the beer distillation section.

Figure 10:
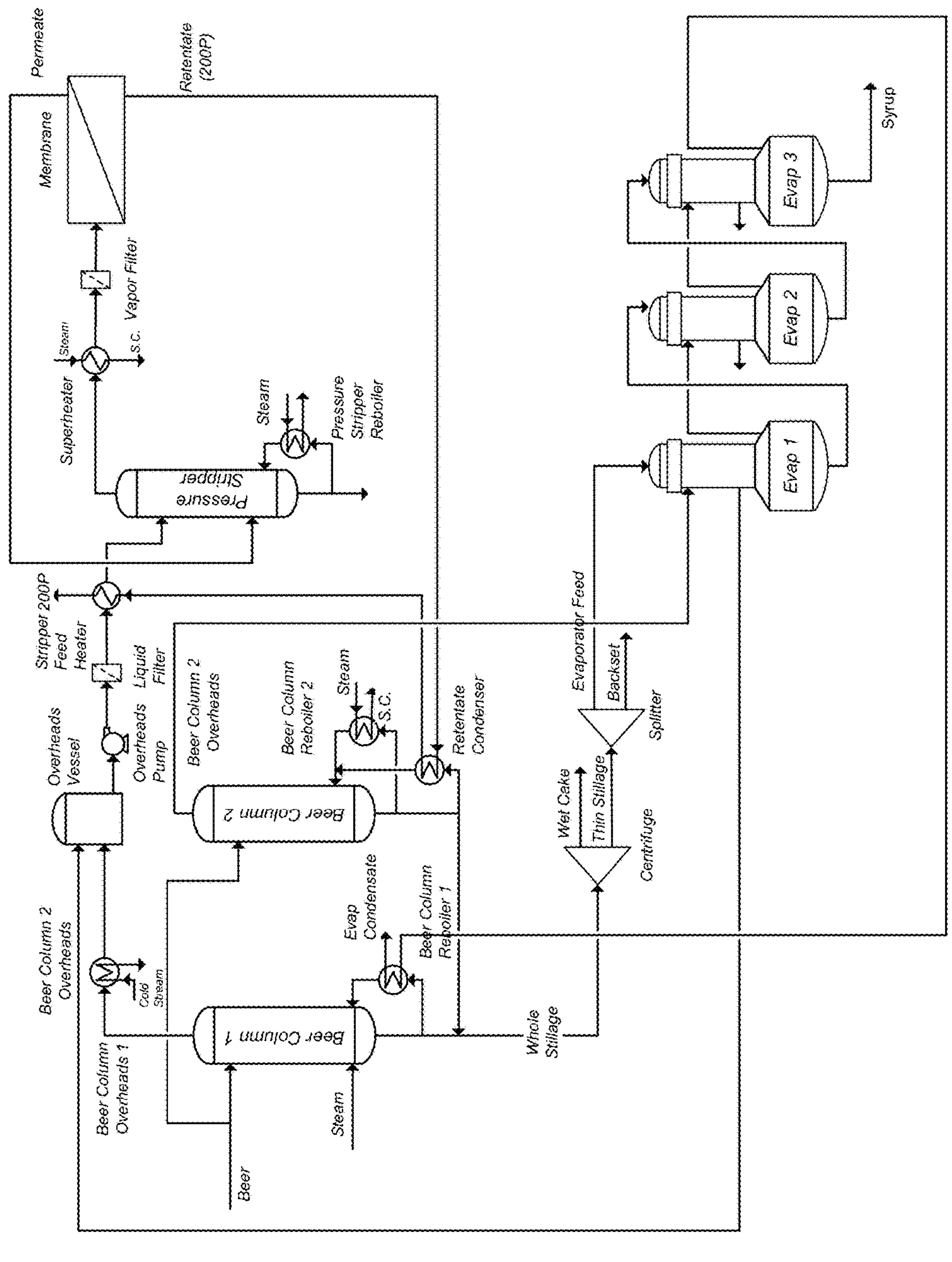
FIG. 10 is a schematic illustration of yet another non-limiting example embodiment of a system for dehydrating a product stream in ethanol production according to the present disclosure.

Referring to FIG. 10, an embodiment is shown with another heat integration of the evaporation section. FIG. 10 shows a system with 2 beer columns, a high pressure stripper and a 3-effect evaporation system characterized by six pressure cascades starting from i) a pressure stripper/membrane system, ii) Beer Column 2, iii) the first evaporator (Evap 1), iv) the second evaporator (Evap 2), v) the third evaporator (Evap 3), and vi) Beer Column 1. Depending on the overall balance any combination of the six cascades is possible. In FIG. 10 the retentate drives Beer Column 2 with the energy of the Beer Column 2 overheads cascading down through the first evaporator (Evap 1), the second evaporator (Evap 2), the third evaporator (Evap 3), and to Beer Column 1.

Figure 11A:
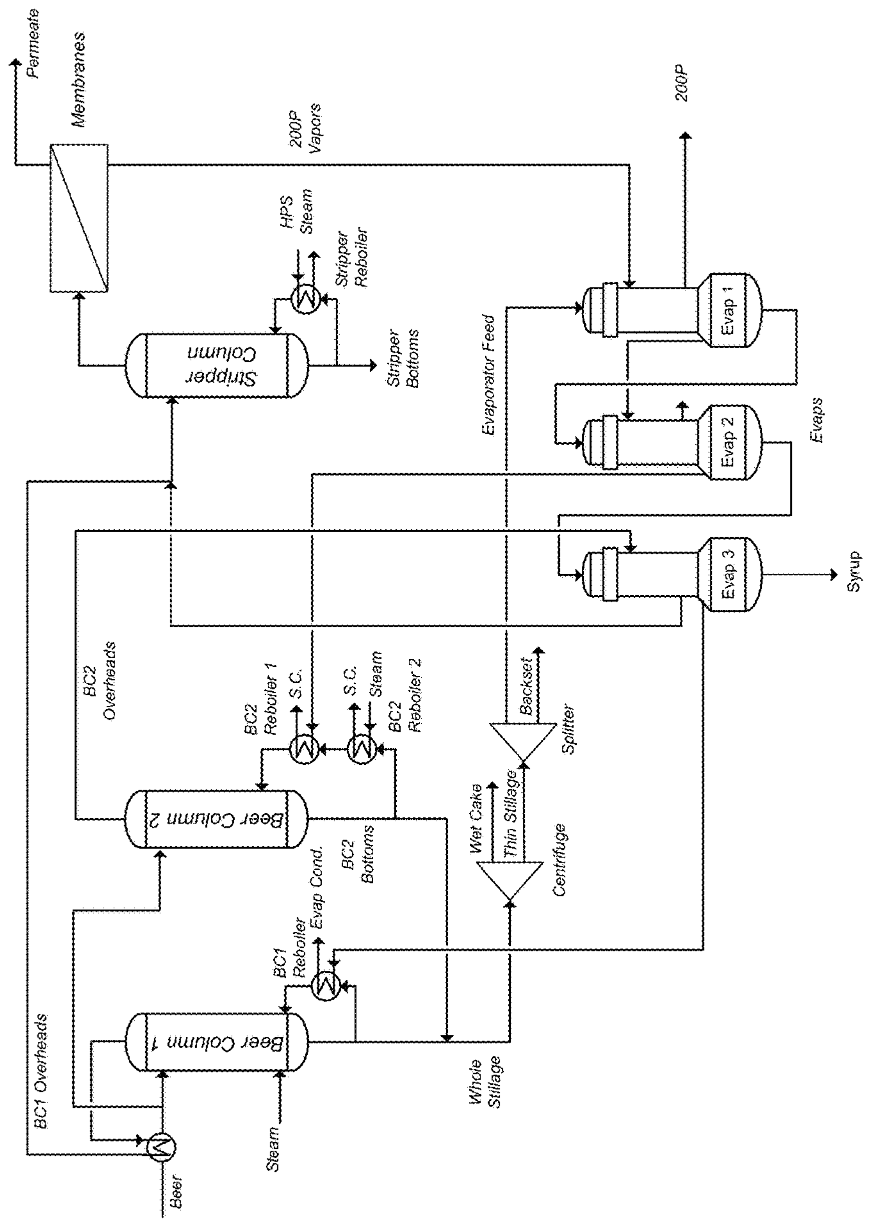
FIGS. 11A-11B are schematic illustrations of yet other non-limiting example embodiments of a system for dehydrating a product stream in ethanol production according to the present disclosure.

FIG. 11A shows another integration following the same principle with the retentate driving the first evaporator (Evap 1), with energy of the steam emerging from the first evaporator (Evap 1) cascading through Beer Column 2, the third evaporator (Evap 3), and to Beer Column 1. The first and second evaporators (Evap 1 and 2) can be operated in parallel or in series. The third evaporator (Evap 3) can be one evaporator or up to six evaporators as shown in FIG. 4. The vapors of the first evaporator (Evap 1), the second evaporator (Evap 2), and the third evaporator (Evap 3) drive Beer Column 1 and/or Beer Column 2 depending on pressure rating. It is possible to add supplemental steam to Beer Column 2 and Beer Column 1 either via the reboiler or DSI, if needed.

Figure 11B:
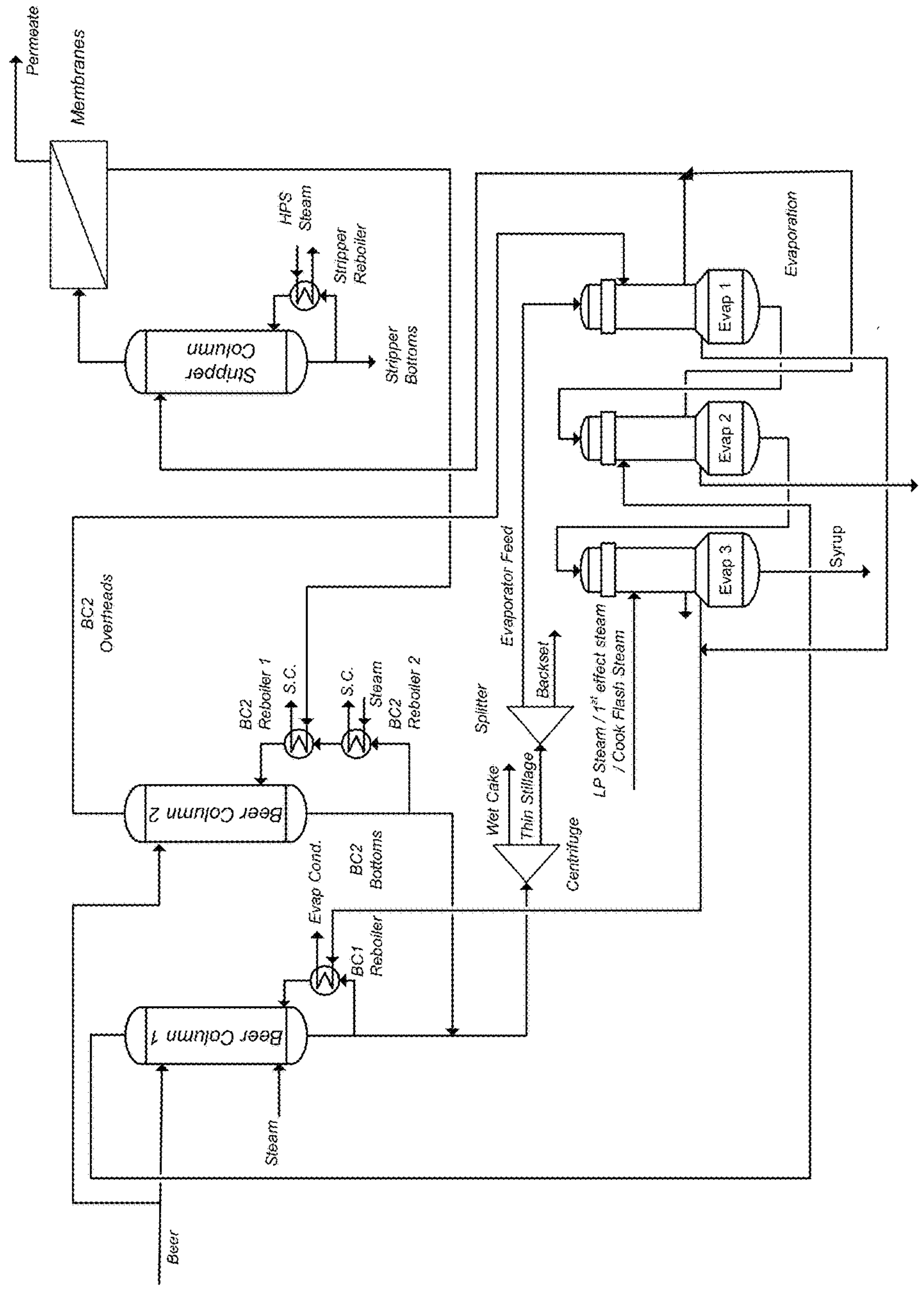

FIG. 11B shows another integration following the same principle with the retentate driving the BC2 Reboiler and energy of the BC2 overheads emerging from BC2 cascading through Evap 1. The third evaporator (Evap 3) can be one evaporator or up to six evaporators in any configuration as shown in FIGS. 4-9 driven by low pressure steam or the first effect vapor. The vapors of the first evaporator (Evap 1), the second evaporator (Evap 2), and the third evaporator (Evap 3) drive Beer Column 1 and/or Beer Column 2 depending on pressure rating. It is possible to add supplemental steam to Beer Column 2 and Beer Column 1 either via the reboiler or DSI, if needed. The Beer Column 1 overhead vapor drives the second evaporator (Evap 2). Beer Column 1 and Beer Column 2 overhead condensates are being fed to the stripper column. The first and second evaporators (Evap 1 and 2) can be operated in parallel or in series.

Figure 12:
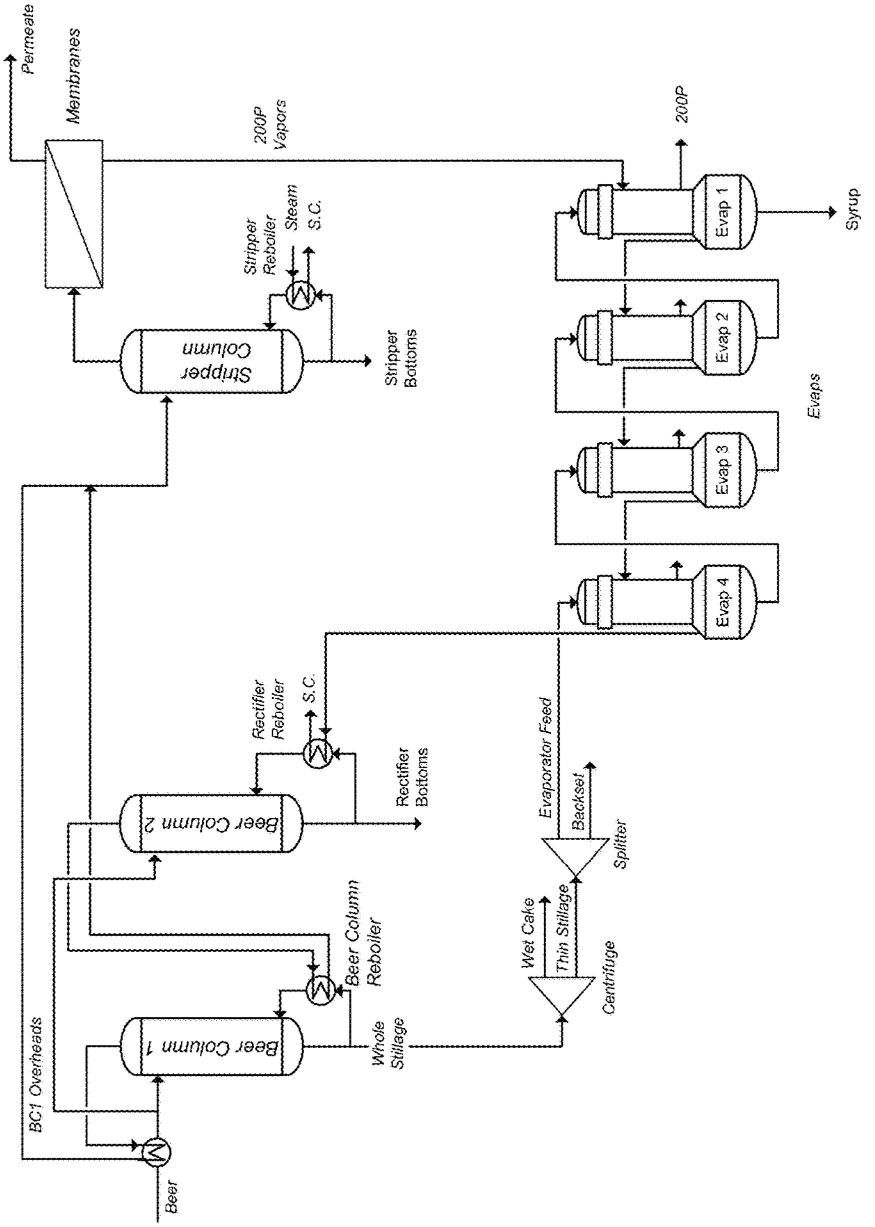
FIG. 12 is a schematic illustration of yet another non-limiting example embodiment of a system for dehydrating a product stream in ethanol production according to the present disclosure.

FIG. 12 shows a 7-cascade system with the retentate heat driving the first evaporator (Evap 1), with energy of the steam emerging from the first evaporator (Evap 1) cascading through the second evaporator (Evap2) to the third evaporator (Evap3), the fourth evaporator (Evap 4), Beer Column 2, and to Beer Column 1.

It should be noted that a partial integration is also part of this application as all or a portion of the evaporator overheads can still be used for re-injection. Those skilled in the art will readily identify a variety of systems that can benefit by replacing molecular sieve units with integrated membrane retrofits according to the present disclosure. For example, such systems are provided in U.S. Pat. No. 7,744,727 and WO 2007/095875, each of which is incorporated by reference herein in its entirety.

Figure 13:
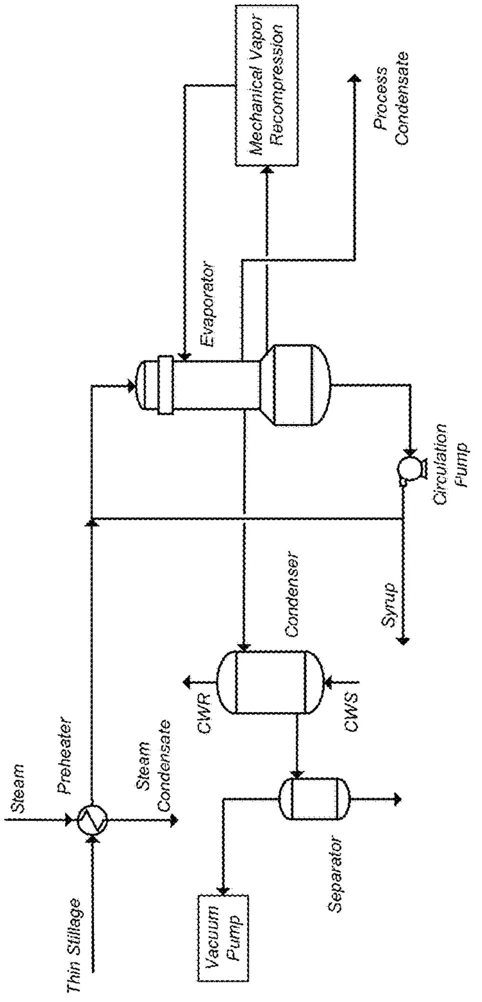
FIG. 13 is a schematic illustration of yet another non-limiting example embodiment of a system for dehydrating a product stream in ethanol production according to the present disclosure.

Referring to FIG. 13, in the illustrated embodiment a mechanical vapor recompression (MVR) unit is added to enhance heat recuperation and drive down the energy consumption of the overall system further. The thin stillage stream in this embodiment is equivalent to the Evaporator Feed illustrated in the previous drawings. Although FIG. 13 shows one evaporator only, in other embodiment, a number of evaporators in parallel or in-series can be used. The liquid stillage is fed into the top of the evaporator. Compressed steam is fed to the side of the evaporator. As the steam condenses, a portion of the stillage liquid is evaporated—this vapor is the feed to the MVR unit. The evaporators can be operating under vacuum. For example, the feed to the MVR typically ranges between 2 and 14.7 psia. The compression ratio of the MVR typically ranges between 1.5 and 10.

In addition to all above embodiments various methods of vapor compression such as Thermal Vapor Compression (TVR) and/or Mechanical Vapor Recompression (MVR) can be added to enhance heat recuperation and drive down the energy consumption of the overall system further. Also heat recovery from dryers, thermal oxidizers, regenerative thermal oxidizers, and combined heat and power (CHP) can be included in the system for dehydrating a product stream in ethanol production according to the present disclosure.

In certain non-limiting embodiments, the system for dehydrating a product stream in ethanol production according to the present disclosure can provide heat integration. One energy intensive step in prior systems is the sequence of “condensation and re-evaporation” of the 190 proof stream prior to dehydration. By replacing molecular sieve units with integrated membrane retrofits according to the present disclosure, energy consumption can be reduced by approx. 50%, for example by approx. 8,000 BTU/gal. In certain non-limiting embodiments, heat is exchanged between the distillation system and the evaporation section. In certain non-limiting embodiments, heat is exchanged between the distillation system and the dryer section. In certain non-limiting embodiments, heat is exchanged—between the distillation system and the RT/TO section. In certain non-limiting embodiments, heat is exchanged between the distillation system and the CHP section. In certain non-limiting embodiments, material is exchanged between the distillation system and the evaporation section. In certain the distillation system is contacted with other sections of the plant for heat integration. For example, such methods for heat integration are provided in U.S. patent application Ser. No. 15/400,546, which is incorporated by reference herein in its entirety.

Figure 14:
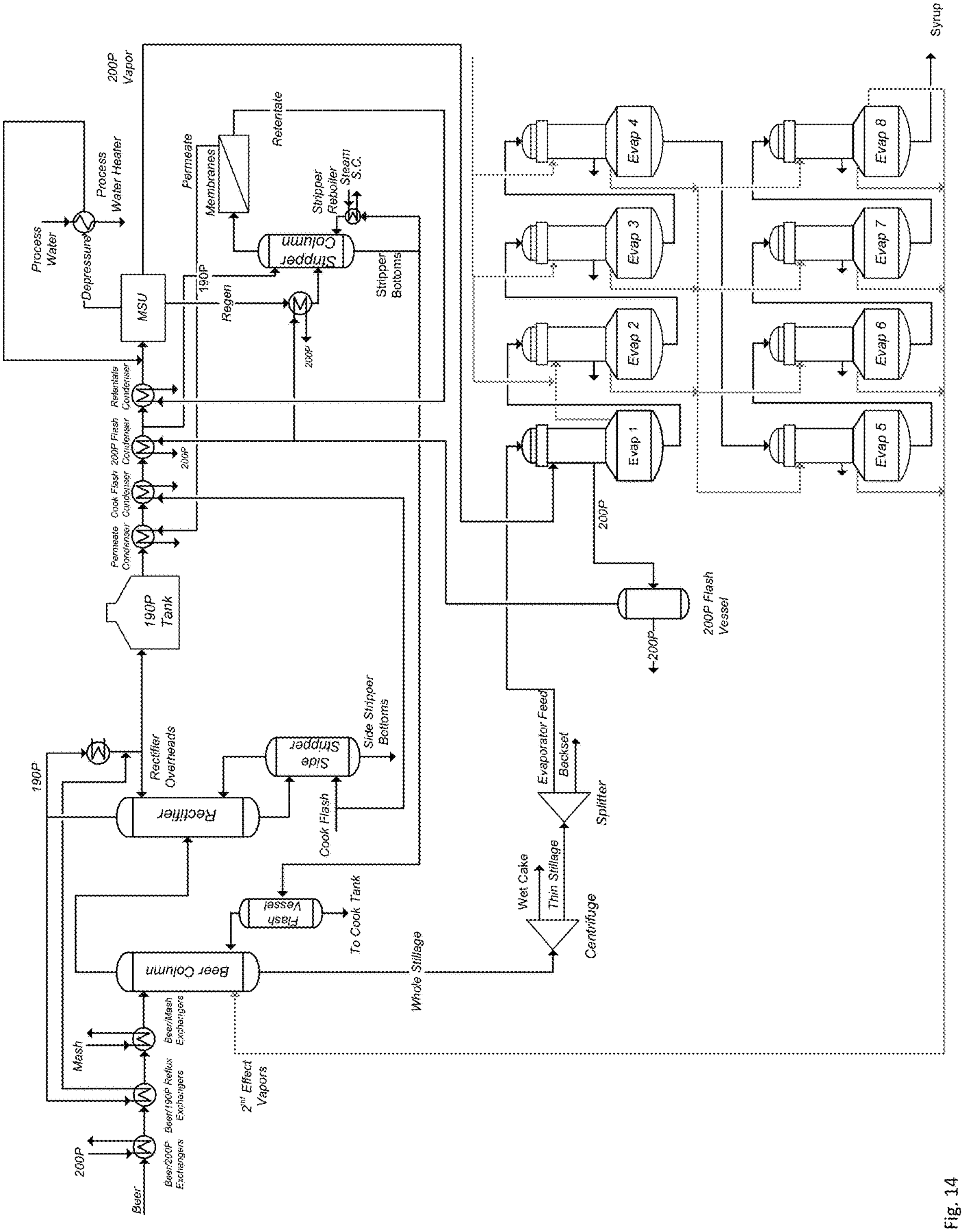
FIG. 14 is a schematic illustration of yet another non-limiting example embodiment of a system for dehydrating a product stream in ethanol production according to the present disclosure.

FIGS. 14-17 illustrate processes and systems for dehydrating a product stream in ethanol production according to another embodiment of the invention. Referring to FIG. 14, in the illustrated embodiment a molecular sieve unit (MSU) is configured to form a product stream and a regenerate stream. In certain non-limiting embodiments, the regenerate stream is treated with a stripper and a membrane system. The illustrated system reduces steam consumption in the beer column by deloading the rectifier/side stripper and by flashing high-pressure stripper bottoms into the beer column. To achieve the steam reduction without sacrificing syrup concentration the vapor emerging from the first evaporator (Evap 1) is re-directed to the second evaporator (Evap 2) eliminating the need for steam supply to the second evaporator (Evap 2). This is in line with the concepts described in this application as effectively a 4-cascade system (e.g., (1) high-pressure MSU, (2) the first evaporator (Evap 1) to the fourth evaporator (Evap 4), (3) the fifth evaporator (Evap 5) to the eighth evaporator (Evap 8), and (4) Beer Column) is converted into a partial 5 cascade system (e.g., (1) high-pressure MSU, (2) the first evaporator (Evap 1), (3) the second evaporator (Evap 2), (4) the fifth evaporator (Evap 5) to the sixth evaporator (Evap 6), and (5) Beer Column). It becomes evident that the concept applies to any reconfiguration of the evaporation as described in FIGS. 6-9.

Referring to FIG. 14, the illustrated embodiment of the system or production plant for ethanol production includes one beer column, a rectifier-side stripper, a molecular sieve unit, a separation system comprising a stripper column and a membrane, and a plurality of evaporators. In the illustrated embodiment, the plurality of evaporators comprise eight evaporators (Evap 1-8). The first evaporator (Evap 1) produces a vegetal steam which is directed to the second evaporator (Evap 2). The second evaporator to the fourth evaporator (Evap 2-4) produce vegetal steam directed into a header feeding the fifth evaporator to the eighth evaporator (Evap 5-Evap 8), each of which produces vegetal steam which is directed to another header driving the beer column. Although FIG. 14 illustrates the system as including eight evaporators, in other embodiments, the system may include two or more evaporators.

Figure 15:
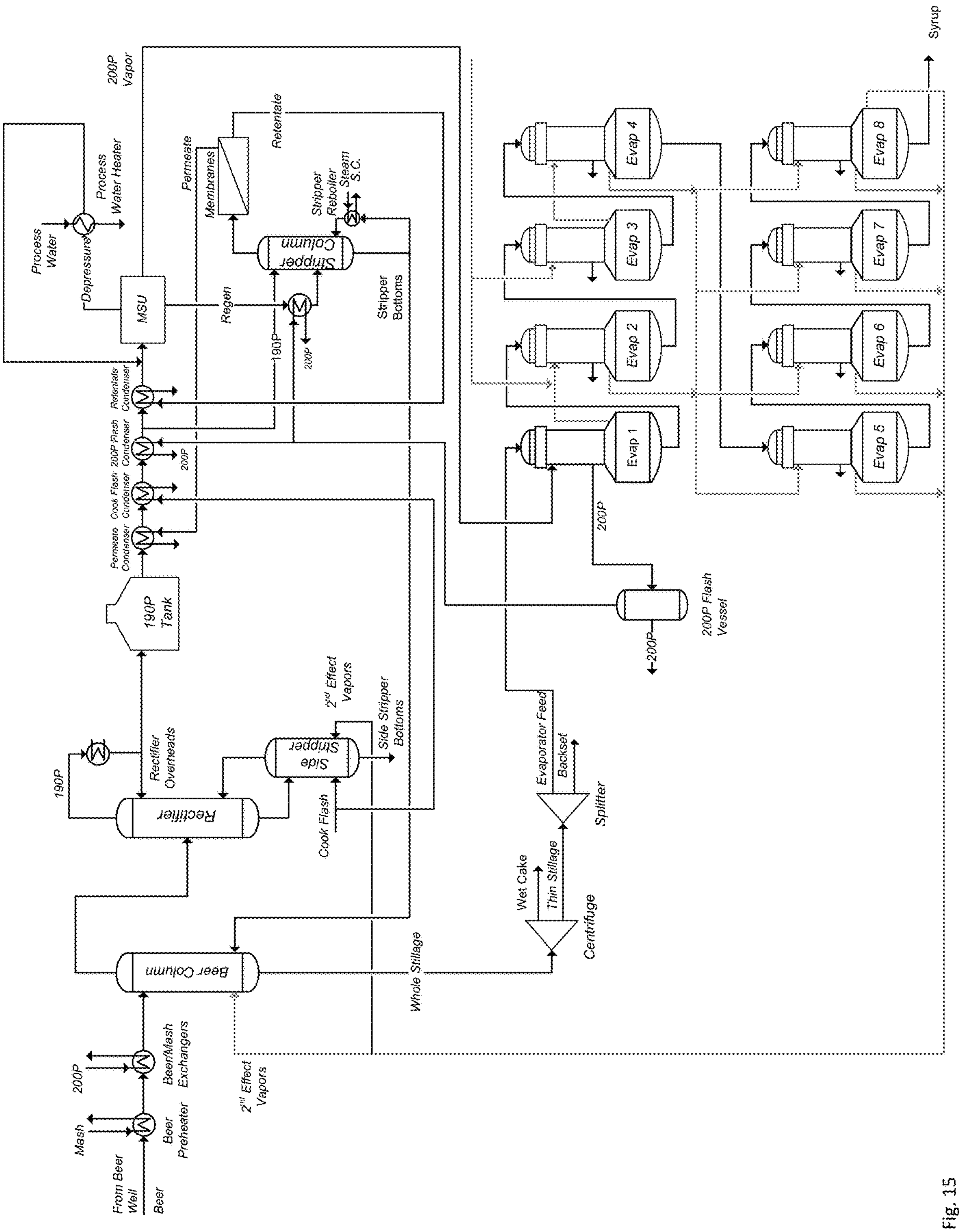
FIG. 15 is a schematic illustration of yet another non-limiting example embodiment of a system for dehydrating a product stream in ethanol production according to the present disclosure.

Referring to FIG. 15, the illustrated embodiment of the system or production plant for ethanol production includes one beer column, a rectifier-side stripper, a molecular sieve unit, a separation system comprising a stripper column and a membrane, and a plurality of evaporators. In the illustrated embodiment, the vegetal steam is forwarded from the first evaporator (Evap 1) to the second evaporator (Evap 2), and from the third evaporator (Evap 3) to the fourth evaporator (Evap 4).

Figure 16:
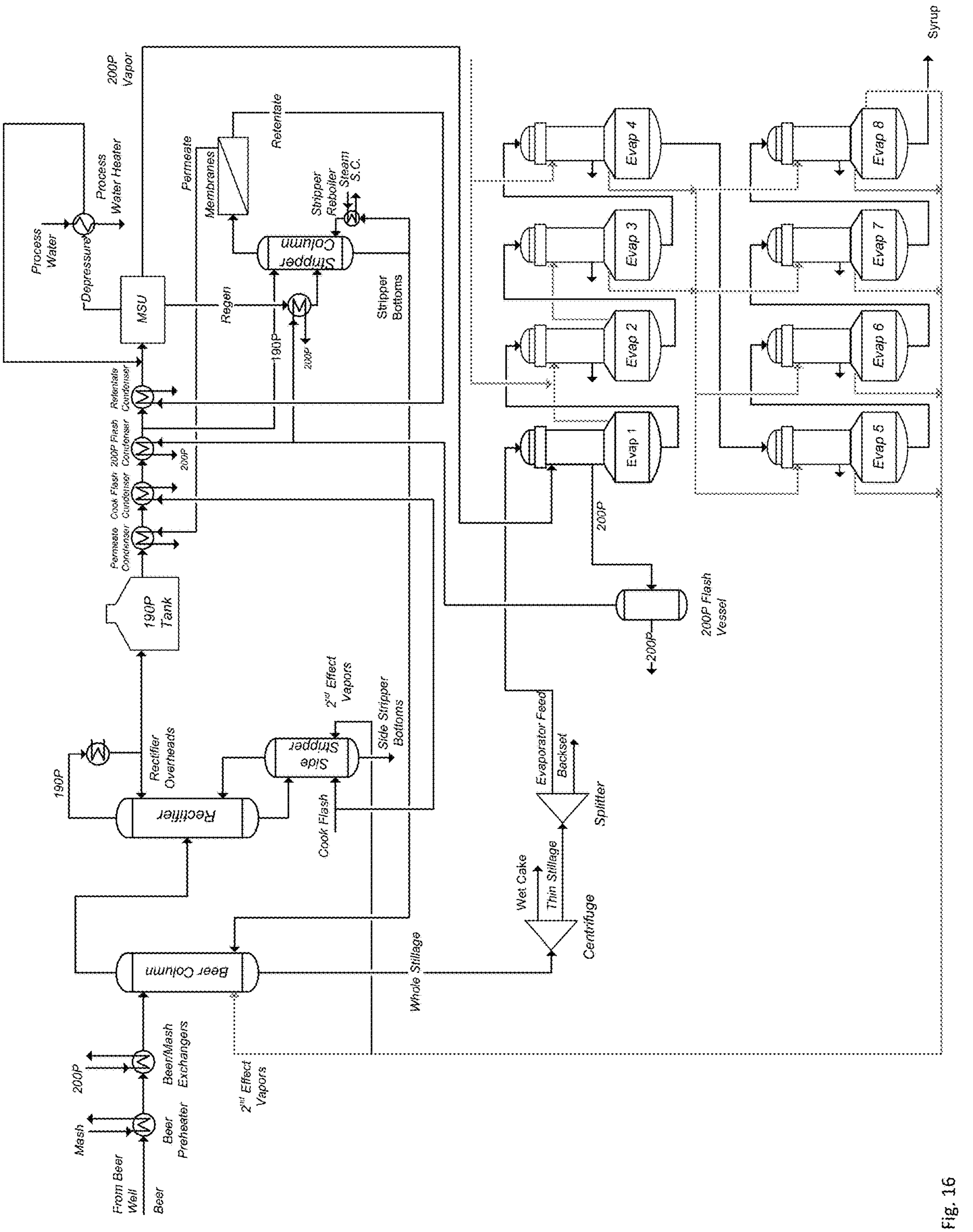
FIG. 16 is a schematic illustration of yet another non-limiting example embodiment of a system for dehydrating a product stream in ethanol production according to the present disclosure.

Referring to FIG. 16, the illustrated embodiment of the system or production plant for ethanol production includes one beer column, a rectifier-side stripper, a molecular sieve unit, a separation system comprising a stripper column and a membrane, and a plurality of evaporators. In the illustrated embodiment, the vegetal steam is forwarded from the first evaporator (Evap 1) to the second evaporator (Evap 2), and from the second evaporator (Evap 2) to the third evaporator (Evap 3).

Figure 17:
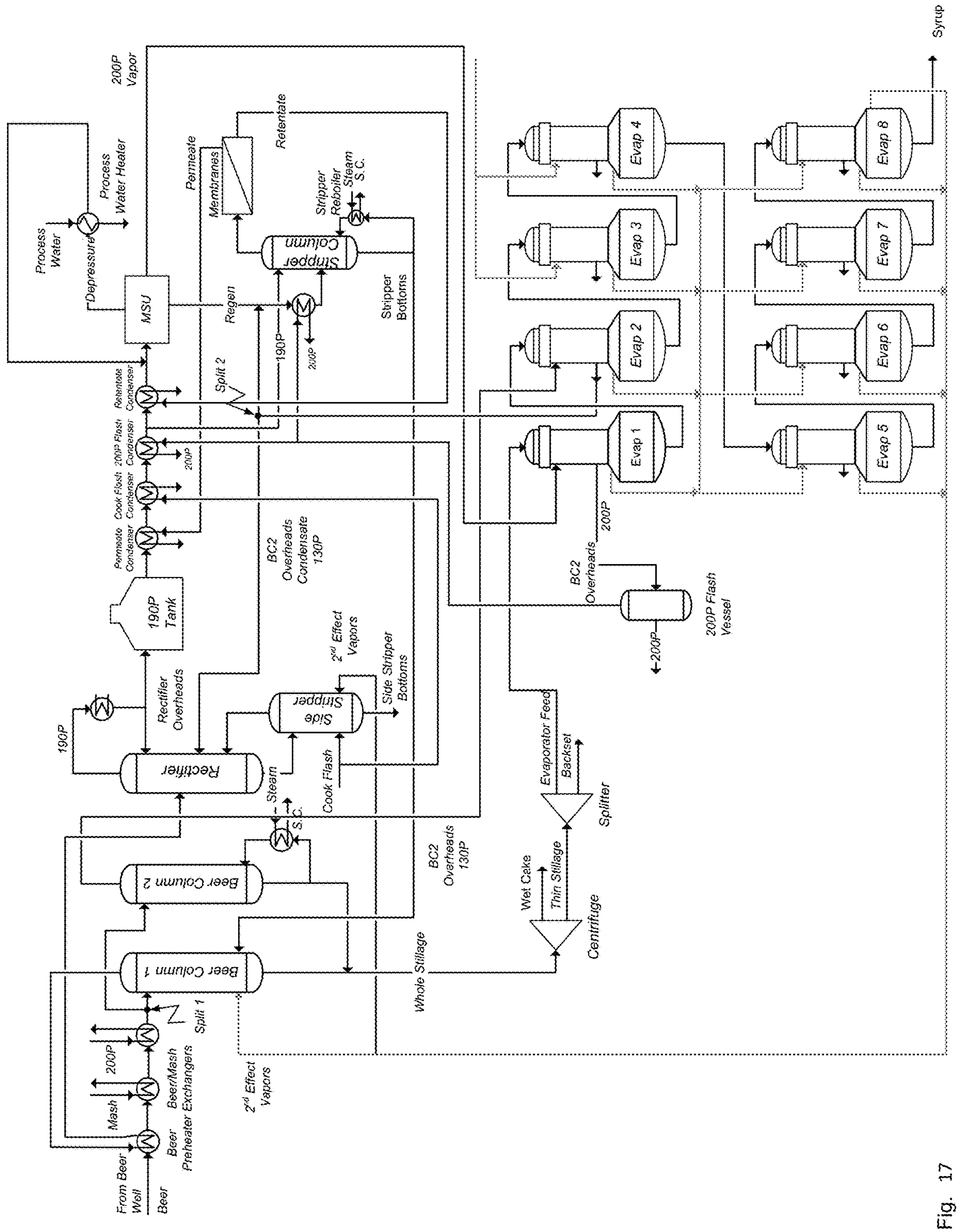
FIG. 17 is a schematic illustration of yet another non-limiting example embodiment of a system for dehydrating a product stream in ethanol production according to the present disclosure.

Referring to FIG. 17, the illustrated embodiment of the system or production plant for ethanol production includes two beer columns, a rectifier-side stripper, a molecular sieve unit, a separation system comprising a stripper column and a membrane, and a plurality of evaporators. In the illustrated embodiment, the separation system comprising the stripper column and the membrane treats the Regen and all or a portion of the Beer Column 2 overheads condensate 130 P. The overall integration can be implemented in different stages by modifying Splits 1 and 2. Split 1 determines how much beer feed is being sent to Beer Column 2 (Maximum 50%), and Split 2 determines how much of the Beer Column 2 overhead is being sent to the rectifier and/or to the separation system comprising the stripper column and the membrane.

Although the foregoing description has necessarily presented only a limited number of embodiments, those of ordinary skill in the relevant art will appreciate that various changes in the processes and systems other details of the examples that have been described and illustrated herein may be made by those skilled in the art, and all such modifications will remain within the principle and scope of the present disclosure as expressed herein. For example, although the present disclosure has presented only a limited number of embodiments of heat integration, it will be understood that the present disclosure is not so limited. It is understood, therefore, that the present inventions are not limited to the particular embodiments disclosed herein, but is intended to cover modifications that are within the principle and scope of the inventions. It will also be appreciated by those skilled in the art that changes could be made to the embodiments above without departing from the broad inventive concept thereof.

In the present description of non-limiting embodiments, other than in in the operating examples or where otherwise indicated, all numbers expressing quantities or characteristics of ingredients and products, processing conditions, and the like—are to be understood as being modified in all instances by the term "about." Accordingly, unless indicated to the contrary, any numerical parameters set forth in the following description are approximations that may vary depending upon the desired properties one seeks to obtain in the processes and systems according to the present disclosure.

The invention is claimed as follows:

1. A solvent production plant, comprising:

a first distillation column;

a second distillation column, operating at a higher pressure than the first distillation column;

a third distillation column;

a fourth distillation column;

a stillage evaporator; and piping, arranged to selectively configure:

the first distillation column to receive a first portion of a feed stream providing a mixture of an organic solvent, water, and solids;

the second distillation column to receive a second portion of the feed stream;

the third distillation column to receive a first solids-freed overhead stream from the first distillation column;

the stillage evaporator to receive and condense a second solids-freed overhead stream from the second distillation column into a condensed stream; and the fourth distillation column to receive the condensed stream from the stillage evaporator.

2. The solvent production plant of claim 1, further comprising:

a molecular sieve unit (MSU) configured to receive an input stream of a first concentration of a solvent and output a product stream with a second concentration of the solvent that is greater concentration than the input stream; and wherein a third solids-freed overhead stream is produced via the third distillation column at the first concentration of the solvent.

3. The solvent production plant of claim 1, further comprising:

a molecular sieve unit (MSU) configured to receive a first input stream and output a regen stream of a higher water concentration than the first input stream; and wherein the piping is arranged for the fourth distillation column to selectively receive the regen stream from MSU.

4. The solvent production plant of claim 1, further comprising:

a membrane configured to receive an input stream and output a product stream of a lower water concentration than the input stream; and wherein piping is arranged for the membrane to selectively receive a fourth solids-freed overhead stream from the fourth distillation column as the input stream.

5. The solvent production plant of claim 1, further comprising:

a molecular sieve unit (MSU) configured to dehydrate a first input stream to produce a product stream of a lower water concentration than the first input stream; and a membrane configured to dehydrate a second input stream to produce a retentate stream of a lower water concentration than the second input stream.

6. A solvent production plant, comprising:

a first distillation column;

a second distillation column;

a third distillation column;

a condenser; and piping, arranged to configure:

the first distillation column to receive a first portion of a feed stream providing a mixture of an organic solvent, water, and solids to produce a first overhead stream with a higher concentration of the organic solvent than the feed stream and a first bottoms stream with a lower concentration of the organic solvent than the feed stream; and the second distillation column to receive a second portion of the feed stream and produce a second overhead stream with a higher concentration of the organic solvent than the feed stream and a second bottoms stream with a lower concentration of the organic solvent than the feed stream;

the condenser to receive and condense the second overhead stream from the second distillation column into a condensed stream including the organic solvent at a higher concentration than the feed stream; and the third distillation column to receive the condensed stream.

7. A solvent production plant, comprising:

a first distillation column;

a second distillation column;

a third distillation column;

a fourth distillation column;

a condenser; and piping, arranged to configure:

the first distillation column to receive a first portion of a feed stream providing a mixture of an organic solvent, water, and solids to produce a first overhead stream with a higher concentration of the organic solvent than the feed stream and a first bottoms stream with a lower concentration of the organic solvent than the feed stream; and the second distillation column to receive a second portion of the feed stream and produce a second overhead stream with a higher concentration of the organic solvent than the feed stream and a second bottoms stream with a lower concentration of the organic solvent than the feed stream;

the condenser to receive and condense the second overhead stream from the second distillation column into a condensed stream including the organic solvent at a higher concentration than the feed stream; and the third distillation column to receive the first overhead stream from the first distillation column.

8. A solvent production plant, comprising:

a first distillation column;

a second distillation column;

a third distillation column;

a fourth distillation column;

a separation system;

a condenser; and piping, arranged to configure:

the first distillation column to receive a first portion of a feed stream providing a mixture of an organic solvent, water, and solids to produce a first overhead stream with a higher concentration of the organic solvent than the feed stream and a first bottoms stream with a lower concentration of the organic solvent than the feed stream; and the second distillation column to receive a second portion of the feed stream and produce a second overhead stream with a higher concentration of the organic solvent than the feed stream and a second bottoms stream with a lower concentration of the organic solvent than the feed stream;

the condenser to receive and condense the second overhead stream from the second distillation column into a condensed stream including the organic solvent at a higher concentration than the feed stream;

the third distillation column to receive the first overhead stream from the first distillation column and produce a third overhead stream with a greater concentration of the organic solvent than the first overhead stream; and the fourth distillation column to receive a regen stream from the separation system, and output a fourth overhead stream, the fourth overhead stream having a greater concentration of the organic solvent than the third overhead stream.

9. A solvent production plant, comprising:

a first distillation column;

a second distillation column;

a bottoms processing system;

a condenser; and piping, arranged to configure:

the first distillation column to receive a first portion of a feed stream providing a mixture of an organic solvent, water, and solids to produce a first overhead stream with a higher concentration of the organic solvent than the feed stream and a first bottoms stream with a lower concentration of the organic solvent than the feed stream; and the second distillation column to receive a second portion of the feed stream and produce a second overhead stream with a higher concentration of the organic solvent than the feed stream and a second bottoms stream with a lower concentration of the organic solvent than the feed stream;

the condenser to receive and condense the second overhead stream from the second distillation column into a condensed stream including the organic solvent at a higher concentration than the feed stream; and the bottoms processing system to receive one or both of the first bottoms stream and the second bottoms stream and produce a vapor stream that is directed back to the first distillation column.

* * * * *